(12) United States Patent
Cox

(10) Patent No.: US 9,567,369 B2
(45) Date of Patent: Feb. 14, 2017

(54) METHOD OF TREATING METASTATIC CANCER

(71) Applicant: James L. Cox, Kirksville, MO (US)

(72) Inventor: James L. Cox, Kirksville, MO (US)

(73) Assignee: A.T. Still University, Kirksville, MO (US)

( * ) Notice: Subject to any disclaimer, the term of this patent is extended or adjusted under 35 U.S.C. 154(b) by 0 days.

(21) Appl. No.: 13/952,140

(22) Filed: Jul. 26, 2013

(65) Prior Publication Data

US 2014/0038902 A1 Feb. 6, 2014

Related U.S. Application Data

(60) Provisional application No. 61/679,426, filed on Aug. 3, 2012.

(51) Int. Cl.
| | | |
|---|---|---|
| *C07K 7/08* | (2006.01) | |
| *C12N 15/63* | (2006.01) | |
| *C07K 14/81* | (2006.01) | |

(52) U.S. Cl.
CPC ............. *C07K 7/08* (2013.01); *C07K 14/8139* (2013.01); *C12N 15/63* (2013.01)

(58) Field of Classification Search
None
See application file for complete search history.

(56) References Cited

U.S. PATENT DOCUMENTS 5,595,756 A * 1/1997 Bally et al. ................... 424/450

FOREIGN PATENT DOCUMENTS

WO WO2005037221 * 4/2005

OTHER PUBLICATIONS

Sporn et al, "Chemoprevention of Cancer," Carcinogenesis, vol. 21 (2000), 525-530.*
Auerbach et al. (Cancer and Metastasis Reviews, 2000, 19: 167-172).*
Gura T (Science, 1997, 278(5340): 1041-1042, encloses 1-5).*
Metastatic cancer.gov (accessed Apr. 17, 2014).*
Hu (PEG-ging peptides, May 2010 Speciality Chemical Magazine).*
Langel 1-3 (Cell-Penetrating Peptides: Processes and Applications, CRC Press, May 29, 2002).*
Yamazaki Katsuhisa et al. "Screening for Apoptosis Inducers in Microbial Products and Induction of Apoptosis by Cytostatin." The Journal of Antibiotics, 1995, vol. 48, No. 10, p. 1138-1140.
Kawada M. et al. "Differential induction of apoptosis in B 16 melanoma and EL-4 lymphoma cells by cytostatin and bactobolin." Jpn J Cancer Res., 1999, 90(2), p. 219-225,(abstract), [online], retrieved from the PubMed, PMID:101189893.
Kawada Manabu et al. "Specific inhibitors of protein phosphatase 2A inhibit tumor metastasis through augmentation of natural killer cells." International Immunopharmacolog, 2003, vol. 3, Issue 2, p. 179-188.
RU 2182598 C2 (NOV ARTIS AG) May 20, 2002, p. 4-9.
Database NCBI: ADT53193.1, Dec. 13, 2010.
Database NCBI: ABE23772.1, Apr. 5, 2006.
Database NCBI: AEU58186.1, Dec. 1, 2011.
Database NCBI: AAQ71425.1, Sep. 3, 2003.
Database NCBI: AAE72335.1, Aug. 8, 2001.
Database NCBI: AAS30848.1, Feb. 20, 2004.
Database NCBI: AAE72341.1, Aug. 8, 2001.
Database NCBI: AAS30855.1, Feb. 20, 2004.
Database NCBI: AAS30858.1, Feb. 20, 2004.
Database NCBI: AEU54591.1, Dec. 1, 2011.
Database NCBI: NP_001099347.1, Apr. 22, 2012.
Database NCBI: AAS30840.1, Feb. 20, 2004.
Database NCBI: AAS30835.1,Feb. 20, 2004.
Database NCBI: AAS30836.1, Apr. 20, 2004.
International Search Authority / FIPS "Notification of Transmittal of The International Search Report and The Written Opinion of The International Searching Authority, or the Declaration" in the matter of PCT/US2013/052486 dated Nov. 28, 2013.
Abeyweera, T.P., Chen, X., et al.; Phosphorylation of a6-Tublin by Protein Kinase Ca Activates Motility of Human Breast Cells; J Biol Chem Jun. 26, 2009; 284(26).
Bo, H., Zhang, S., et al.; Upregulation of Wnt5a promotes epithelial-to-mesenchymal transition and metastasis of pancreatic cancer cells; BMC Cancer, 2013, vol. 13:496; doi:10.1186/1471-2407-13-496.
El-Andaloussi, S., Jarver, P., et al.; Cargo-dependent cytotoxicity and delivery efficacy of cell-penetrating peptides: a comparative study; Biochem J (2007) doi:10.1042/BJ200070507.
Konduri, S.D., Yanamandra, N., et al.; Modulation of cystatin C expression impairs the invasive and tumorigenic potential of human glioblastoma cells; Oncogene (2002) vol. 21:8705-8712; Nature Publishing Group.
Kopitz, C., Anton, M.; et al.; Reduction of Experimental Human Fibrosarcoma Lung Metastasis in Mice by Adenovirus-Mediated Cystatin C Overexpression in the Host.
Qi, H., Sun, B., et al.; Wnt5a promotes vasculogenic mimicry and epithelial-mesenchymal transition via protein kinase Ca in epithelial ovarian cancer. Oncology Reports (2014) vol. 32:771-119.
Sokol, J.P., Neil, J.R., et al.; The use of cystatin C to inhibit epithelial-mesenchymal transition and morphological transformation stimulated by transforming growth factor-β. Breast Cancer Research (2005) vol. 7:R844-R853 doi10.1186/bcr1212.
Wegiel, B., Jiborn, T., et al.; Cystatin C is Downregulated in Prostate Cancer and Modulates Invasion of Prostate Cancer Cells via MAPK/Erk and Androgen Receptor Pathways. PLoSone (2009) vol. 4:11:e7953.

(Continued)

*Primary Examiner* — James H Alstrum Acevedo
*Assistant Examiner* — Tara Martinez
(74) *Attorney, Agent, or Firm* — Quarles & Brady LLP

(57) ABSTRACT

A method of treating metastatic cancer, comprising the steps of (a) treating a metastatic cancer patient with an isolated therapeutic Cystatin C peptide, and (b) observing a reduction in tumor burden is disclosed.

16 Claims, 5 Drawing Sheets

(56) References Cited

OTHER PUBLICATIONS

Yap, L.F., Ahmad, M., et al.; Oncogenic effects of WNT5A in Epstein-Barr virus-associated nasopharyngeal carcinoma. International Journal of Oncology (2014) vol. 44: 1774-1780.

International Search Authority / Notification Concerning Transmittal of International Preliminary Report on Patentabaility (Chapter I of the Patent Cooperation Treaty) and Written Opinion of the International Searching Authority in the matter of PCT/US2013/052486 dated Feb. 15, 2015.

* cited by examiner

Control – 0time.

Control-24 hours.

Peptide- 0 time.

Peptide- 24 hour.

SEQUENCE LISTING

```
<160> NUMBER OF SEQ ID NOS: 25

<210> SEQ ID NO 1
<211> LENGTH: 5
<212> TYPE: PRT
<213> ORGANISM: Homo sapiens

<400> SEQUENCE: 1

Gln Val Val Ala Gly
1               5

<210> SEQ ID NO 2
<211> LENGTH: 5
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 2

Gln Xaa Val Xaa Gly
1               5

<210> SEQ ID NO 3
<211> LENGTH: 5
<212> TYPE: PRT
<213> ORGANISM: Homo sapiens

<400> SEQUENCE: 3

Gln Val Val Ala Gly
1               5

<210> SEQ ID NO 4
<211> LENGTH: 5
<212> TYPE: PRT
<213> ORGANISM: Mus musculus

<400> SEQUENCE: 4

Gln Leu Val Ala Gly
1               5

<210> SEQ ID NO 5
<211> LENGTH: 16
<212> TYPE: PRT
<213> ORGANISM: Mus musculus

<400> SEQUENCE: 5

Tyr Arg Lys Gln Leu Val Ala Gly Val Asn Tyr Phe Phe Asp Val His
1               5                   10                  15

<210> SEQ ID NO 6
<211> LENGTH: 16
<212> TYPE: PRT
<213> ORGANISM: Homo sapiens
```

<400> SEQUENCE: 6

Ala Arg Lys Gln Ile Val Ala Gly Val Asn Tyr Phe Leu Asp Val Glu
1               5                   10                  15

<210> SEQ ID NO 7
<211> LENGTH: 16
<212> TYPE: PRT
<213> ORGANISM: Rattus norvegicus

<400> SEQUENCE: 7

Ala Arg Lys Gln Leu Val Ala Gly Ile Asn Tyr Tyr Leu Asp Val Glu
1               5                   10                  15

<210> SEQ ID NO 8
<211> LENGTH: 16
<212> TYPE: PRT
<213> ORGANISM: Mus musculus

<400> SEQUENCE: 8

Ala Arg Lys Gln Leu Val Ala Gly Val Asn Tyr Phe Phe Asp Val Glu
1               5                   10                  15

<210> SEQ ID NO 9
<211> LENGTH: 16
<212> TYPE: PRT
<213> ORGANISM: Bos taurus

<400> SEQUENCE: 9

Ala Arg Lys Gln Val Val Ser Gly Met Asn Tyr Phe Leu Asp Val Glu
1               5                   10                  15

<210> SEQ ID NO 10
<211> LENGTH: 16
<212> TYPE: PRT
<213> ORGANISM: Homo sapiens

<400> SEQUENCE: 10

Ala Tyr Gln Gln Ile Val Gly Gly Val Asn Tyr Tyr Phe Asn Val Lys
1               5                   10                  15

<210> SEQ ID NO 11
<211> LENGTH: 16
<212> TYPE: PRT
<213> ORGANISM: Homo sapiens

<400> SEQUENCE: 11

Ala Arg Glu Gln Thr Phe Gly Gly Val Asn Tyr Phe Phe Asp Val Glu
1               5                   10                  15

<210> SEQ ID NO 12
<211> LENGTH: 16
<212> TYPE: PRT
<213> ORGANISM: Rattus norvegicus

<400> SEQUENCE: 12

Val Gln Lys Gln Val Val Ala Gly Thr Lys Phe Phe Phe Asp Val Ile
1               5                   10                  15

<210> SEQ ID NO 13
<211> LENGTH: 16
<212> TYPE: PRT
<213> ORGANISM: Bitis arietans

<400> SEQUENCE: 13

```
Ala Gln Ser Gln Val Val Ser Gly Val Lys Tyr Tyr Leu Met Met Glu
1               5                   10                  15

<210> SEQ ID NO 14
<211> LENGTH: 16
<212> TYPE: PRT
<213> ORGANISM: Homo sapiens

<400> SEQUENCE: 14

Tyr Lys Thr Gln Val Val Ala Gly Thr Asn Tyr Tyr Ile Lys Val Arg
1               5                   10                  15

<210> SEQ ID NO 15
<211> LENGTH: 16
<212> TYPE: PRT
<213> ORGANISM: Rattus norvegicus

<400> SEQUENCE: 15

Tyr Lys Ser Gln Val Val Ala Gly Gln Ile Leu Phe Met Lys Val Asp
1               5                   10                  15

<210> SEQ ID NO 16
<211> LENGTH: 16
<212> TYPE: PRT
<213> ORGANISM: Mus musculus

<400> SEQUENCE: 16

Tyr Lys Thr Gln Val Val Ala Gly Gln Asn Leu Phe Ile Lys Ile Asp
1               5                   10                  15

<210> SEQ ID NO 17
<211> LENGTH: 16
<212> TYPE: PRT
<213> ORGANISM: Homo sapiens

<400> SEQUENCE: 17

Phe Lys Ser Gln Val Val Ala Gly Thr Asn Tyr Phe Ile Lys Val His
1               5                   10                  15

<210> SEQ ID NO 18
<211> LENGTH: 16
<212> TYPE: PRT
<213> ORGANISM: Rattus norvegicus

<400> SEQUENCE: 18

Phe Arg Arg Gln Val Val Ala Gly Thr Asn Phe Phe Ile Lys Val Asp
1               5                   10                  15

<210> SEQ ID NO 19
<211> LENGTH: 16
<212> TYPE: PRT
<213> ORGANISM: Bitis arietans

<400> SEQUENCE: 19

Phe Lys Ser Gln Leu Val Ala Gly Lys Asn Tyr Phe Ile Lys Val Gln
1               5                   10                  15

<210> SEQ ID NO 20
<211> LENGTH: 16
<212> TYPE: PRT
<213> ORGANISM: Bitis arietans

<400> SEQUENCE: 20

Phe Arg Ser Gln Val Val Ala Gly Met Asn Tyr Leu Ile Lys Val Gln
```

```
<210> SEQ ID NO 21
<211> LENGTH: 16
<212> TYPE: PRT
<213> ORGANISM: Artificial Sequence
<220> FEATURE:
<223> OTHER INFORMATION: Consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 21

Xaa Lys Arg Xaa Gln Val Val Ala Gly Xaa Asn Tyr Phe Xaa Asp Glu
1               5                   10                  15

<210> SEQ ID NO 22
<211> LENGTH: 16
<212> TYPE: PRT
<213> ORGANISM: Artificial Sequence
<220> FEATURE:
<223> OTHER INFORMATION: Cystatin type II consensus

<400> SEQUENCE: 22

Ala Arg Lys Gln Val Val Ala Gly Val Asn Tyr Phe Phe Asp Val Glu
1               5                   10                  15

<210> SEQ ID NO 23
<211> LENGTH: 16
<212> TYPE: PRT
<213> ORGANISM: Artificial Sequence
<220> FEATURE:
<223> OTHER INFORMATION: Cystatin type I consensus

<400> SEQUENCE: 23

Phe Lys Ser Gln Val Val Ala Gly Thr Asn Tyr Phe Ile Lys Val Asp
1               5                   10                  15

<210> SEQ ID NO 24
<211> LENGTH: 33
<212> TYPE: PRT
<213> ORGANISM: Artificial Sequence
<220> FEATURE:
<223> OTHER INFORMATION: Cystatin peptide linked to penetratin

<400> SEQUENCE: 24

Arg Gln Ile Lys Ile Trp Phe Pro Asn Arg Arg Met Lys Trp Lys Lys
1               5                   10                  15

Ala Tyr Arg Lys Gln Leu Val Ala Gly Val Asn Tyr Phe Phe Asp Val
            20                  25                  30

His

<210> SEQ ID NO 25
<211> LENGTH: 16
<212> TYPE: PRT
```

```
<213> ORGANISM: Artificial Sequence
<220> FEATURE:
<223> OTHER INFORMATION: Penetratin

<400> SEQUENCE: 25

Arg Gln Ile Lys Ile Trp Phe Pro Asn Arg Arg Met Lys Trp Lys Lys
1               5                   10                  15
```

METHOD OF TREATING METASTATIC CANCER

CROSS-REFERENCE TO RELATED APPLICATIONS

This application claims priority from U.S. provisional patent application Ser. No. 61/679,426 filed Aug. 3, 2012, incorporated by reference herein.

STATEMENT REGARDING FEDERALLY SPONSORED RESEARCH OR DEVELOPMENT

Not applicable.

BACKGROUND

The cystatins belong to a large superfamily of proteins, many of which inhibit cysteine proteases of the C1 class (cathepsins). Virtually all organisms produce one or more members of the cystatin superfamily, often multiple types. Basically, there are three major cystatin families, the types I, II, and III cystatins and a number of cystatin-related protein families (1). While new physiological processes are being tied to the cystatins, it is their links to several human pathologies which command the most attention. The use of Cystatin C as a marker of kidney function in various disease states is very well studied (2). Cystatin has also been linked to both cancer and Alzheimer's disease (3,4). While the cystatin link to Alzheimer's is still being worked out, a number of important studies have proposed cystatins as potent inhibitors of various cancers.

Metastasis or the spread and growth of cancer is the primary reason for cancer treatment failure and loss of life from cancer. Metastasis is very difficult to treat because metastatic cancers are usually resistant to cancer therapies and metastatic cancers spread systemically and relentlessly in the cancer patient, outstripping any treatment strategy. Currently, there are no purely anti-metastatic agents in clinical use. We first found that Cystatin C, a natural cysteine protease inhibitor, exhibits anti-metastatic effects on melanoma, one of the most metastatic of all cancers (5). We found that Cystatin C genetic overexpression inhibits melanoma cell migration and invasion (6). Another study by our laboratory showed Cystatin C overexpression inhibits metastasis by inducing higher levels of melanoma cell death in lungs of animals after melanoma cell injection (7). Work by other groups showed that Cystatin C is also anti-metastatic for a number of other cancers (glioblastoma, breast, prostate, and colorectal (cystatin D) when overexpressed (8,9,10,11). We believe that critical anti-metastatic effects derived from cystatin must be able to account for increased apoptosis of metastatic cancer cells and/or cancer cell migration inhibition. Of course intact cystatin, as a cysteine protease inhibitor, may also function as an inhibitor of cathepsin-type proteases and hence may partially inhibit invasion for some cancers. We do not believe, however, the protease inhibitory activity of cystatin is critical to cystatin's anti-metastatic action because of the partial inhibition of cancer cell metastasis shown by synthetic cysteine protease inhibitors (12).

Needed in the art an the improved method of treating metastatic cancer with Cystatin C.

SUMMARY OF THE INVENTION

We are the first to find (described herein) that a small, internal peptide fragment of Cystatin C inhibits the activity of protein kinase C (PKC), a critical enzyme which helps drive the metastatic propensity of many cancer types (13). For the purposes of this application, we refer to this internal Cystatin C fragment, and other internal fragments with the same function, as the "therapeutic Cystatin C peptide".

Inhibition of PKC through various drugs has already been shown in the literature to block the metastasis of different cancers through signaling pathways linked to cancer cell survival and cell migration (14). PKC drives pathways linked to cancer cell survival but it has not been possible to use PKC inhibitors as drugs for cancer treatment because of the problem of multiple PKC isoforms which make current PKC targeted drugs too toxic for the patient (15).

We believe the PKC isoform specificity of the therapeutic peptide [the peptide inhibits PKC $\alpha$ and $\epsilon$, because these isoforms of PKC phosphorylate MARCKS protein] greatly increases the utility of the peptide for therapeutic use. The therapeutic peptide is also a very weak inhibitor of papain, the plant derived and prototypical cysteine protease (20% inhibition at 160 uM) (16). Therefore, we do not expect significant inhibitor action of this peptide against tumor cysteine proteases and hence this mechanism is not a major contributor to the anti-metastatic action of this peptide.

Based on the discovery above, we envision that the therapeutic Cystatin C peptide can be used to inhibit tumor, tumor malignancy and/or tumor invasion. Thus, in its first aspect, the present invention relates to methods of treating metastatic cancer, which comprises the steps of (a) treating a metastatic cancer patient with an isolated therapeutic Cystatin C peptide, and (b) observing a reduction in tumor burden.

Therapeutic Cystatin C peptide comprises a peptide sequence selected from a group consisting of SEQ ID NO: 5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23 and the modifications, derivatives, fragments, combinations, and hybrids thereof that retain the activity of inhibiting the activity of protein kinase C (PKC).

Specifically, the therapeutic Cystatin C peptide comprises the sequence QXVZG (SEQ ID NO:2), wherein X is selected from a group consisting of V, I, L and T and Z is selected from a group consisting of A, S, G and Q. Preferably, the therapeutic Cystatin C peptide comprises the sequence QVVAG (SEQ ID NO:3) or QLVAG (SEQ ID NO:4).

The therapeutic Cystatin C peptide may be additionally attached to an uptake peptide, such as a penetratin peptide comprising SEQ ID NO:25, or additionally attached to a polyethylene glycol (PEG).

The peptide is delivered is delivered by a route selected from a group consisting of intravenous delivery, intradermal delivery, intratumoral delivery, intrathecal delivery and intramuscular delivery. Preferably, the peptide is delivered intravenously.

The method is effective if the tumor burden is reduced by at least 25% after one month of daily treatment.

In its second aspect, the present invention relates to a chemotherapeutic compound comprising an isolated therapeutic Cystatin C peptide.

In its third aspect, the present invention relates to a DNA sequence encoding an isolated therapeutic peptide. The DNA sequence may additionally comprise a plasmid vector. Preferably, the DNA sequence comprises a plasmid vector which enables mammalian expression.

DESCRIPTION OF THE INVENTION

In General

Figure 1:
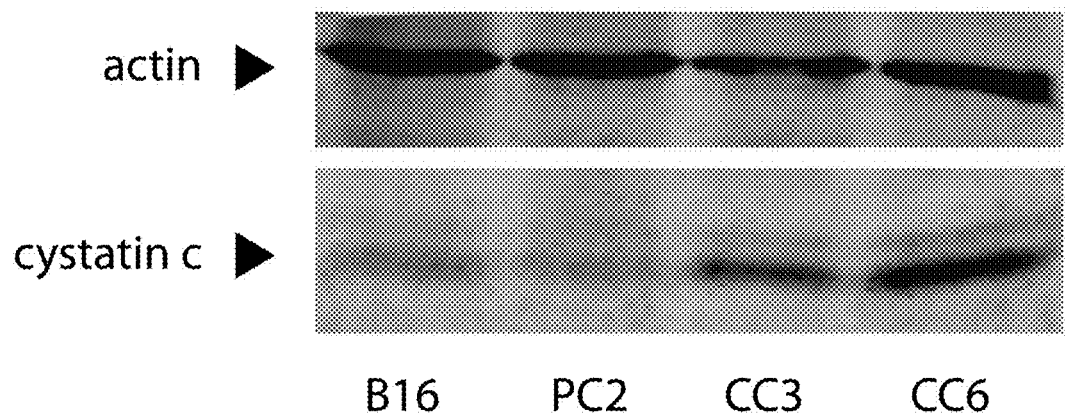
FIG. 1 is an image of western blot analysis of 24 hour spent, serum free media (10× conc) from cells in culture demonstrated several clones over-produced Cystatin C. Clone 6 (cc6) was taken for further analysis and compared to control clone pc2 (pcDNA3 plasmid transfected).
Figure 2:
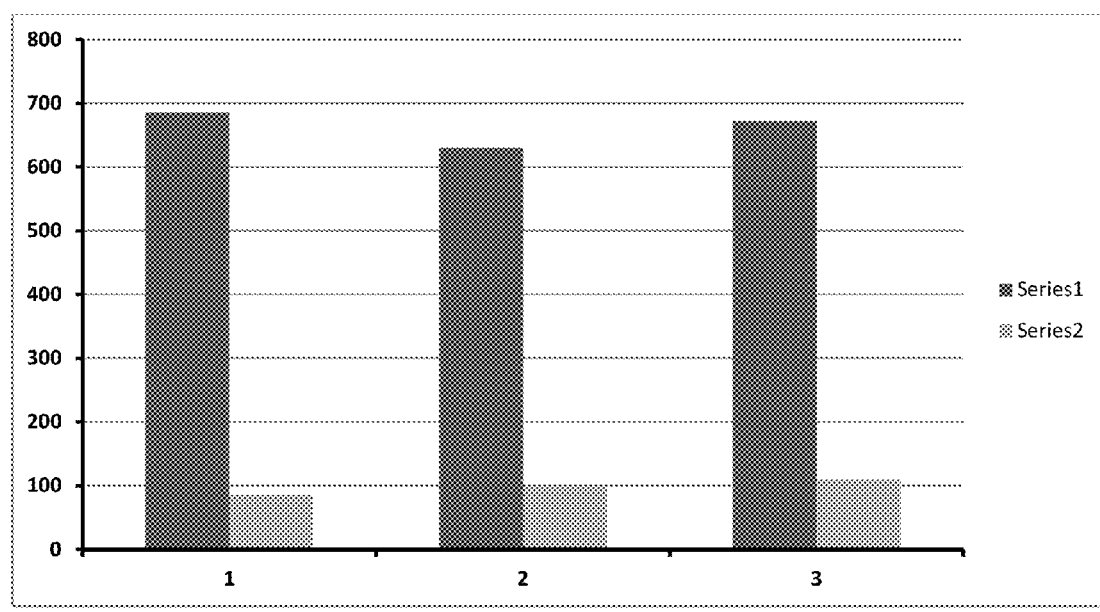
FIG. 2 shows the relative migration of a cystatin overexpressing clone (cc6) versus control plasmid clone (pc2). The migration of B16 melanoma cells which overexpress Cystatin C showed a significant inhibition of migration (~80%) compare to control plasmid transfected in Boyden chamber-type assays.
Figure 3:
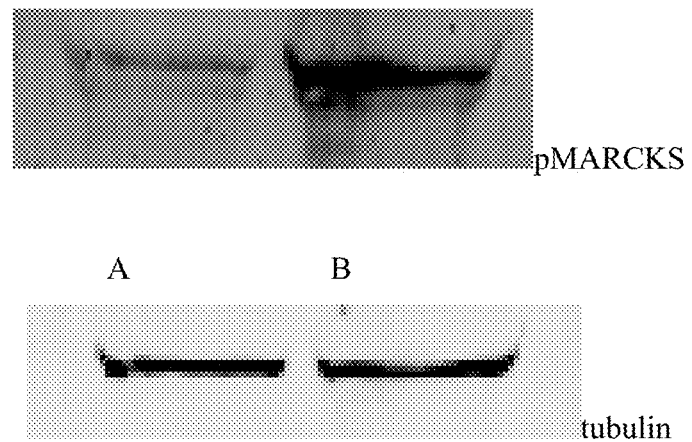
FIG. 3 shows the average level of MARCKS phosphorylation as determined with phospho-antibody probing. The level is about 3-5 fold less for murine Cystatin C overexpressing (clone cc6) B16F10 melanoma cells (lane A).
Figure 4:
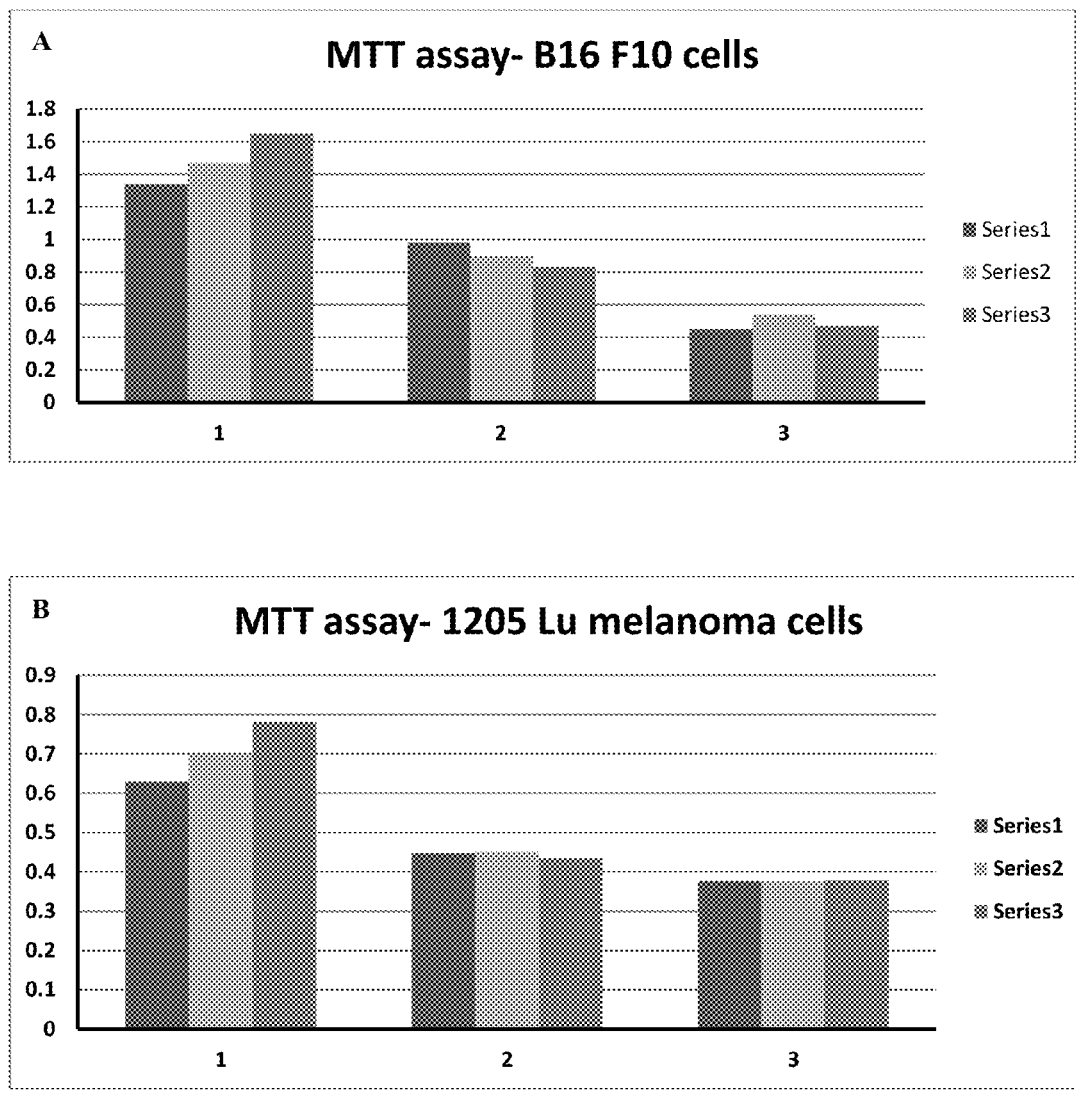
FIG. 4 shows purified peptide (penetratin linked to active peptide, 33 mer) was added directly to culture wells at 10 uM with equivalent volume of water added to control wells. The growth inhibition of B16 melanoma cells (control lane 1) was 40% inhibited when peptide was added at day 1 only (lane 2) versus 68% if the peptide was added on days 1-3 of the growth experiment (lane 3) (FIG. 4a). This experiment showed the peptide by itself was inhibitory to B16 melanoma cell growth and that inhibition was more effective after multiple additions. We also tested the peptide on the metastatic human melanoma 1205 Lu cells grown in culture under identical conditions as for the B16 melanoma cells (FIG. 4b). The results show the peptide significantly inhibits the growth of human 1205 Lu melanoma cell line (lane 2, 1 time addition), (lane 3, day 1-3 addition).
Figure 5:
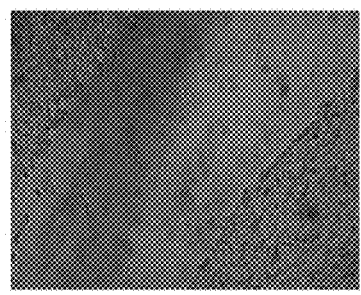
FIG. 5 is a set of confluent B16 melanoma cell scratches+/−peptide at different times.
Figure 5:
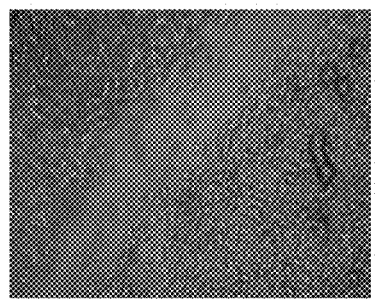
Figure 5:
Figure 5:
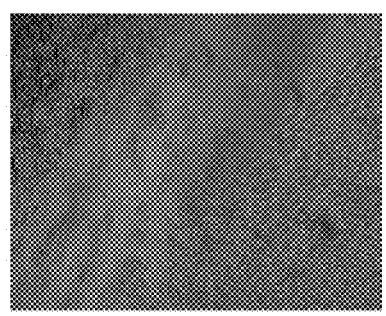

The present invention relates to a small internal peptide fragment of Cystatin C or a homologous peptide or related peptide or corresponding DNA fragment from Cystatin C or other cystatins. The fragment, termed the "therapeutic Cystatin C peptide", inhibits protein kinase C activity and protein kinase C related pathways. This is a newly discovered function of cystatins that we discovered and that is not related to the common function of cysteine protease inhibition by the cystatins. The present invention relates to this PKC-active, Cystatin C-derived therapeutic peptide or homologues or peptide mimetic compounds or DNA/RNA coding similar sequences to inhibit tumor, tumor malignancy and/or tumor invasion.

Prior work has suggested native cystatin delivery might be useful for therapy of metastatic disease. We have improved on the prior work by describing a completely new mechanism of action for a segment of cystatin that allows us to predict which internal peptide fragments will be therapeutically suitable and link this peptide to a delivery system (preferably a peptide-16 amino acid penetratin sequence) which can dramatically improve the effectiveness of the anti-metastatic peptide agent. Additional advantages of this therapeutic peptide are that the active peptide sequence is derived from a natural protein, it is totally degraded in the body to non-toxic amino acids, and small peptides are only weakly immunogenic, if at all.

Peptide of the Present Invention

Preferably, the active peptide is between 12 and 18 amino acids in length, more preferably 16 amino acids in length, and includes the most highly conserved sequence among all cystatins, the "QVVAG" sequence (SEQ ID NO:1), in native-sequence or in variant form, as well as derivatives, fragments, and analogs from any source, whether natural, synthetic, or recombinant, provided that at least 50%, at least 60%, at least 70% of the peptide's activity of inhibiting PKC is retained. Preferably, at least 80% or 90% of such activity is retained.

The peptide of the present invention also includes the 'QVVAG' sequence with conservative substitutions. The term "conservative substitution" as used herein denotes the replacement of an amino acid residue by another, biologically similar residue with respect to hydrophobicity, hydrophilicity, cationic charge, anionic charge, shape, polarity and the like. Examples of conservative substitutions include the substitution of one hydrophobic residue such as isoleucine (I), valine (V), leucine (L), norleucine (Nle) alanine (A), cysteine (C), glycine (G), phenylalanine (F), proline (P), tryptophan (W), tyrosine (Y) or methionine (M) for another, or the substitution of one polar residue for another, such as the substitution of arginine (R) for lysine (K), glutamic acid (E) for aspartic acid (D), or glutamine (Q) for asparagines (N), and the like. Neutral hydrophilic amino acids, which can be substituted for one another, include asparagines (N), glutamine (Q), serine (S) and threonine (T).

The term "conservative substitution" also includes the use of a substituted or modified amino acid in place of an unsubstituted parent amino acid provided that substituted peptide has similar proteases property to the QVVAG sequence. By "substituted" or "modified" the present invention includes those amino acids that have been altered or modified from naturally occurring amino acids. As such, it should be understood that in the context of the present invention, a conservative substitution is recognized in the art as a substitution of one amino acid for another amino acid that has similar properties.

It is envisioned that at least the second amino acid or the fourth amino acid, or both of the sequence QVVAG are substitutable, as long as at least 50%, at least 60%, at least 70% of the peptide's activity of inhibiting PKC is retained after the substitution(s). Preferably, at least 80% or 90% of such activity is retained after the substitution(s). In this application, the QVVAG sequence and its suitable conservative substitutions is defined in form of the "QXVZG" sequence (SEQ ID NO:2), in which the amino acids X and Z are substitutable.

In one embodiment, the amino acid in the X position is V, I, L or T. In another embodiment, the amino acid in the Z positions is A, S, G or Q. In a preferred embodiment, the X is V or L and Z is A.

In one preferred embodiment, the "QXVZG" sequence is QVVAG (SEQ ID NO:3) or QLVAG (SEQ ID NO:4). For example, in a mouse, the therapeutic Cystatin C peptide comprises the sequence of YRKQLVAGVNYFFDVH (SEQ ID NO:5).

The cystatins are present in almost all organisms. We found that clearly identifiable cystatins are present in rice and corn plants with sequences similar to those described here. Tables I and II, below, are cystatin sequences and conserved sequences that are found in 1, 2 and 3 cystatin types. This is the 'QVVAG' region found at the first hairpin loop of the cystatin protein. (Stefin is another name for cystatin type I (20)). Any of the peptides listed in Tables I and II are appropriate peptides of the present invention and are "therapeutic Cystatin C peptides". Note the consensus sequences listed in Table II which would allow one skilled in the art to create appropriate peptides and allow substitutions and changes from naturally occurring sequences.

In another aspect, the present invention is a nucleotide sequence encoding a peptide of the present invention.

We believe the minimal sequence for activity is QVVAG, allowing for conservative substitutions for the first V (i.e., I or L). Preferably, one would have a peptide of between 10 and 16 amino acids in length and the sequence would be a naturally occurring Cystatin C sequence. However, we envision that one could place the minimal 'QVVAG' sequence within a larger peptide.

All of the sequences in Table I are internal peptides of type II (the first 8 sequences) or type I (the last 8 sequences). Both the type I and type II cystatin types have been shown to inhibit metastasis. In fact, the puff adder venom cystatin has been shown to inhibit melanoma metastasis in a purified form. The puff adder sequence is a little divergent but is covered within consensus sequence.

The type II cystatins arose from gene duplication of the type I or II cystatin to include 3 copies of the cystatin protein in the same megaprotein. Two of the three copies inhibit cathepsins and the other copy diverged to inhibit calpain. To the extent that the consensus sequence is present it may also be used as a source for the peptide. The type III have been shown to inhibit angiogenesis but not metastasis directly.

The consensus sequence in Table II is a generalized consensus as it represents the most common amino acid residue at each site. The hyphen refers to designation of weak consensus at that site. 9 out of 16 residues are a perfect match with the consensus with the I (isoleucine) for V (valine) as a conservative substitution. Other conservative substitutions may also work for this peptide but that data set does not exist. So for example it is known cystatin D behaves similarly in regards to metastatic inhibition and it has both an I and a G substituted within the QVVAG.

TABLE I

Cystatin peptide sequences in the QVVAG region
(about residues 50-66 of 120 total for type II cystatin)

| Sequence | Source |
| --- | --- |
| ARKQIVAGVNYFLDVE (SEQ ID NO: 6) | human Cystatin C |
| ARKQLVAGINYYLDVE (SEQ ID NO: 7) | rat Cystatin C |
| ARKQLVAGVNYFFDVE (SEQ ID NO: 8) | mouse Cystatin C |
| ARKQVVSGMNYFLDVE (SEQ ID NO: 9) | bovine Cystatin C |
| AYQQIVGGVNYYFNVK (SEQ ID NO: 10) | human cystatin D |
| AREQTFGGVNYFFDVE (SEQ ID NO: 11) | human cystatin S |
| VQKQVVAGTKFFFDVI (SEQ ID NO: 12) | rat cystatin S |
| AQSQVVSGVKYYLMME (SEQ ID NO: 13) | puff adder cystatin |
| YKTQVVAGTNYYIKVR (SEQ ID NO: 14) | human cystatin A |
| YKSQVVAGQILFMKVD (SEQ ID NO: 15) | rat cystatin A |
| YKTQVVAGQNLFIKID (SEQ ID NO: 16) | mouse cystatin A |
| FKSQVVAGTNYFIKVH (SEQ ID NO: 17) | human stefin B |
| FRRQVVAGTNFFIKVD (SEQ ID NO: 18) | rat stefin B |
| FKSQLVAGKNYFIKVQ (SEQ ID NO: 19) | bovine stefin B |
| FRSQVVAGMNYLIKVQ (SEQ ID NO: 20) | bovine stefin C |

TABLE II

Cystatin Type II peptide sequences in the QVVAG region

| Peptide Sequence | Source |
| --- | --- |
| -K/R-QVVAG-NYF-D/E (SEQ ID NO: 21) | consensus sequence* |
| ARKQVVAGVNYFFDVE (SEQ ID NO: 22) | cystatin type II consensus |
| FKSQVVAGTNYFIKVD (SEQ ID NO: 23) | cystatin type I consensus |
| YRKQLVAGVNYFFDVH (SEQ ID NO: 5) | Experimental murine peptide** |

*11/16 matches, with conserved K or R at position 2 and D or E at position 16.
**Therapeutic peptide used in these studies derived from mouse Cystatin C with the first A substituted by Y for cloning purposes.

Formulation of the therapeutic cystatin peptide contemplates the native cystatin peptide sequence and all modifications, derivatives, fragments, combinations, and hybrids thereof that retain at least 50%, at least 60%, at least 70% of the peptide's activity to inhibit PKC. Preferably, at least 80% or 90% of the activity is retained.

The therapeutic peptide may be further modified or attached to a carrier. The Cystatin C peptide or its therapeutic moiety can be synthesized by any methods known in the art.

In some embodiments, modifications to improve the therapeutic peptide life-time such as addition of polyethylene glycol (PEG) or similar purpose modifying agent. Peptide N-terminal or C-terminal chemical modifications which might serve to improve in vivo stability of the peptide to proteases.

In some embodiments, peptide modifications can be made to increase stability in regards to in vivo degradation. Capping of the N-terminus by acylation is the preferred method. Amidation of the carboxy-terminus of the peptide to protect from plasma peptidases is also possible.

In the examples below, the cystatin peptide has also been covalently linked to a cell-penetrating peptide (penetratin) for more efficient delivery into cells (17). The delivery of this active peptide to cancer cells, by nature of its size and cell penetratin peptide would be greatly improved over delivery of intact cystatin protein, which happens to contain the active peptide we describe, due to the greater molecular size and less efficient uptake of intact cystatin by cells. Delivery of intact cystatin as a protein or in a DNA form or by viral vector will always suffer from inefficiency of delivery and, hence, expression in an intact host.

Therefore, in a preferred version of the present invention, one would link the therapeutic peptide to an "uptake peptide," preferably the Penetratin peptide. The examples below disclose a minor derivative of the original Penetratin sequence. (Essentially, we included within the sequence for penetratin a proline which the authors found blocked cell nuclear trafficking of the penetratin—only cytoplasmic localization was observed with this penetratin subtype, (17)). There are several papers which disclose cell penetrating peptides for anti-cancer peptide delivery (21,22). However, our invention is the first to inhibit metastasis through inhibiting migration and cancer cell survival derived from cystatin. Commercial use of Penetratin for delivery is in clinical trials (23).

Method of the Present Invention

In one embodiment, the present invention is a method of using the therapeutic peptide described above to inhibit tumor malignancy and tumor invasion.

In a preferred embodiment, one would use the peptide therapeutic in the following manner: In the CDG Therapeutics clinical trial referenced above, subjects received p28 peptide three times a week administered or delivered into a vein for four weeks (NCT00914914 sponsor: CDG Therapeutics, Inc. (2009) A Phase I Trial of p28). We anticipate intravenous injection as the most likely route for systemic administration of the peptide. Other delivery methods can be used as well, including but not limited to administering the peptide therapeutic intramuscularly, orally, intrathecally, intradermally, intratumorally, intralesionally, intranasally, intracerebrally (intraparenchymally), intracerebroventricularly, intranasally, intraocularly, intraarterially, topically, transdermally, subcutaneously, via an aerosol, infusion, bolus injection, implantation device, sustained release system etc., either alone or conjugated to a suitable therapeutic carrier.

Other clinical uses of penetrating peptides include uses for treatment of myocardial infarction, glioblastoma treatment, and treatment of stroke (Johnson R M et al. in Methods Mol Biol 683, 535-51. 2011, Fialho A M et al. Glioblastoma mutiforme: novel therapeutic approaches ISRN Neurol 2012:642345 Epub 2012, Xigen).

One could also deliver the Cystatin C peptide in a DNA form or sequence either as part of an expression plasmid or virus vector which expresses the therapeutic peptide from an incorporated DNA sequence which is engineered into the plasmid or virus expression system either alone or as part of a fusion peptide.

In some embodiments, the DNA sequence encoding a Cystatin C peptide or at least a functional portion of a Cystatin C peptide is inserted into a plasmid. The DNA sequence can be cDNA or genomic DNA. The plasmid can be any DNA molecule that is capable of autonomous replication within a host cell, either extrachromosomaily or as part of the host cell chromosomes. The starting plasmids are commercially available, are publicly available on an unrestricted basis, or can be constructed from such available plasmids. In certain instances, as will be apparent to the ordinarily skilled artisan, other suitable plasmids known in the art may be used as well.

In some embodiments, the vector for delivering the Cystatin C peptide comprises the DNA sequence of a Cystatin C peptide or at least a function portion of a Cystatin C peptide. The vector is characterized in that it comprises a nucleotide sequence wherein a gene coding for a Cystatin C peptide is linked to a promoter.

The DNA sequence of the present invention can also include a promoter which is recognized by the host organism and is operably linked to the Cystatin C peptide encoding nucleic acid. Promoters are untranslated sequences located upstream from the start codon of a structural gene (generally within about 100 to 1000 bp) that control the transcription and translation of nucleic acid under their control, including inducible and constitutive promoters. Inducible promoters are promoters that initiate increased levels of transcription from DNA under their control in response to some change in culture conditions, e.g. the presence or absence of a nutrient or a change in temperature. At this time a large number of promoters recognized by a variety of potential host cells are well known.

The DNA sequence of the present invention can include a nucleic acid sequence encoding a signal Cystatin C peptide. Further, the DNA sequence can include additional nucleic acids which encode reporter products to monitor levels of gene expression, or encode peptide tags which can be visualized using known methods in the art to monitor levels of peptide expression. The DNA sequence of the present invention can also comprise expression and cloning vectors which may contain a selection gene or a selectable marker that encodes a protein necessary for the survival or growth of a host cell transformed with the vector. Typical selection genes encode proteins that confer resistance to antibiotics or other toxins and complement auxotrophic deficiencies.

Preferably, the DNA sequence encoding a Cystatin C peptide or at least a functional portion of a Cystatin C peptide is inserted into a plasmid for use as a mammalian expression vector. For example, the gene encoding the Cystatin C peptide is inserted into a virus expression vector such as adenovirus (for example, pcDNA-3) for mammalian cell expression.

Examples of cancers or malignancy tumors that can be treated by the peptide of the present invention include, but are not limited to, breast cancer, colorectal cancer, lung cancer, prostate cancer, colon cancer, ovarian cancer, cervical cancer, gastrointestinal cancer, pancreatic cancer, glioma, glioblastoma, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, ovarian cancer, neuroblastoma, myeloma, various types of head and neck cancer, lymphoma cancer, leukemia, acute lymphoblastic leukemia, acute myeloid leukemia, Ewing sarcoma and peripheral neuroepithelioma, and other carcinomas, lymphomas, blastomas, sarcomas, and leukemias.

In one embodiment of the present invention, one would measure the clinical efficiency of the peptide. For measurement of clinical therapeutic efficiency of the peptide there are many imaging modalities that might be employed. One example would be MRI imaging of the tumor region in a patient to determine the relative growth or spread of the cancer before and after delivery of the peptide to a patient. An alternative would also be PET scan because of the high sensitivity of this imaging modality to cancer in the patient. Antibody methods of tumor detection are also possible, and although specialized techniques are required for their preparation, they are specific for certain cancers and hence within the realm of detection techniques that could be envisioned. One would consider the method of the present invention to be a success if tumor growth were halted, inhibited or reversed Inhibition of growth of the metastatic tumor by at least 25% preferably 50%, is a successful embodiment.

For melanoma examination a sentinel lymph node biopsy could be used to determine the peptide effect on status of the spread of the cancer. These biopsies are used for tumor staging in melanoma but could also give a critical window into progression during treatment with the described peptide.

Based upon in vitro testing of the purified peptide, one embodiment of the present invention would provide at least a 25% decrease in tumor burden in a cancer patient and significant reduction in metastasis after application of the peptide in 1-3 infusions of an effective dose.

EXAMPLES

Therapeutic Applications of the Peptide

It is envisioned that application of the described peptide could open up new avenues for therapeutic treatment of cancer, since up until now agents have not been targeted against metastasis, the major cause of death from cancer. Therapeutic applications of the described peptide could include intravenous delivery or infusion for systemic distribution of the peptide into a cancer patient. Systemic delivery of the therapeutic peptide may be necessary for cases of metastatic disease in the cancer patient. Periodic infusion or continuous infusion of the peptide could also augment other standard cancer therapies for different cancers, particularly if the cancer has become metastatic. Additive or synergistic effects of simultaneous treatment with the described peptide and other accepted anti-cancer therapies would be expected due to the unique cellular targeting of the peptide to cancer cell pathways which drive metastasis and tumor cell survival.

Another major application would be adjunctive use of the therapeutic peptide following surgical removal of a primary tumor in cases where the tumor removal is not 100% (curative) or residual disease after tumor removal is suspected. In these cases, adjunctive therapy could either be with systemic delivery of the peptide alone or in conjunction with other anti-cancer agents.

Another application of the peptide could include either intravenous injections or infusions or bolus injection of a physiological based solution of the therapeutic peptide into the tumor region within the cancer patient. This might allow higher concentrations of the peptide to be delivered more directly into the tumor environment for more efficient tumor uptake. The dose and frequency of peptide delivery may have to be empirically determined on a cancer by cancer basis due to the variability between different cancers.

In cases where direct injection of a physiological based solution (i.e. physiological saline or other suitable osmotic solution) of the peptide into the tumor or tumor region could be used for delivery, it is envisioned that peptide dosing of a particular cancer with multiple injections may be required, depending upon the biological half-life of the specific peptide or peptide mimetic composition. More stable forms or derivatives of the peptide such as those containing D-isomer amino acids, or other suitably modified peptides or peptide mimetics may require fewer injections to achieve similar therapeutic doses and results.

There may also be instances, particularly in skin cancer patients with surface lesions, where direct contact of a peptide containing solution, either administered by a patch or other suitable delivery device or reservoir could be implemented as the peptide in its basic formulation is able to directly penetrate into cells and may be delivered by means other than blood supply to organs or tissues.

Alternatively, a small pump containing the peptide may be surgically inserted below the skin into a region of the body known to be a major site of tumor spread or systemic delivery for a particular cancer type to 'head off' metastatic cancer cells as they arise from residual or un-resected cancerous tumors.

Other possible scenarios for use of the peptide are with nanoparticle delivery systems which may allow pill formulation such that the peptide survives the digestive system intact. Nanoparticles or nano-materials may also incorporate tumor targeting motifs to enhance targeting of the therapeutic peptide to the tumor cells. Any efficient delivery system which can bring about sustained, therapeutic levels of the peptide systemically or in the region of the cancer should be the therapeutic objective during cancer therapy with the described peptide.

Materials and Methods

B16F10 melanoma cells were obtained from the ATCC. Human 1205 Lu metastatic melanoma cell line was received from Robert Baer, PhD, a collaborator with our laboratory here at ATSU. Growth was in RPMI 1640 media supplemented with FBS (10%) and penicillin, streptomycin, amphotericin antibiotics (1%) (Sigma). Cells were maintained in a humidified incubator at 37° C. with 5% $CO_2$.

Isolation of Cystatin Clones

The Cystatin C cDNA was amplified from B16F10 melanoma cells by PCR amplification of reverse transcribed total RNA isolated from B16 F10 melanoma cells in culture. The primers used for the amplification were derived from 5' and 3' sequences for murine Cystatin C from Solem et al. (18). The PCR product corresponding to the expected size was agarose gel purified and ligated into pcDNA3 expression plasmid for further analysis. The plasmid was sent to for sequence analysis at the University of Chicago and the sequence analysis produced a cDNA sequence which exactly matched murine Cystatin C cDNA sequence (19). Transfection of the cystatin plasmid or pcDNA3 plasmid was carried out with Lipofectamine™ reagent (Invitrogen) by the manufacturer's instructions. Isolated cell colonies, which had grown following Geneticin® (1 mg/ml) selection were trypsized in glass cloning rings and transferred to multi-well tissue culture dishes for expansion in culture.

Western Blot Analysis

For analysis of B16 melanoma proteins, melanoma cell cultures were lysed with lysis buffer and extracts were centrifuged at 10K rpm for 5 minutes. Protein was measured by Lowry assay and 40 ug of protein was loaded per lane on 10% SDS-PAGE gels for analysis. After electrophoresis, the proteins were transferred to PVDF membranes which were first blocked with 2% BSA in TBST buffer. Primary antibodies were added at 1:2000 dilution in TBST and incubated at room temperature for 1 hour, with rocking, or, for phospho-antibodies, overnight at 4° C. Secondary antibodies were used at 1:20,000 dilution for the LiCor detection system (infrared). Cystatin C antibody was a goat polyclonal antibody (Pierce). The pMARCKS antibody was S 152/156 rabbit polyclonal (Cell Signaling) and the tubulin used was from DSHB (Iowa City).

Migration Assay

The migration of clone cc6 was tested in Boyden-type chambers which allow quantitation of cells which migrate through 8 um pores in a filter which do not allow the passage of non-migrating cells. Cells (2×10$^4$) are placed into the top well of the Boyden chamber in cell culture media while media plus bFGF chemotactic factor (25 ng/ml) is placed into the lower well of the chamber. Quantitation is through direct microscopic counting of 10-20 fields of crystal violet stained cells per filter.

Cystatin Peptide

The cystatin peptide linked to the uptake peptide (penetratin) was synthesized by Peptide 2.0 company and purified to 96% purity. The amino acid sequence of the peptide is RQIKIWFPNRRMKWKKAYRKQLVAGVNYFFDVH (SEQ ID NO:24) with the first 16 amino acids RQIKIWF-PNRRMKWKK (SEQ ID NO:25) corresponding to the penetratin uptake peptide sequence and the final 16 amino acids YRKQLVAGVNYFFDVH (SEQ ID NO:5) corresponding to the Cystatin C active peptide with a single A (alanine) separating the two sequences (not necessary for functionality but arose during separate DNA cloning experiments, not reported here). The dried peptide product was resuspended in sterile, deionized water to 1 mM concentration and kept frozen between uses.

MTT Assays

The growth of B16F10 melanoma cells by the MTT method was performed with the addition of 10 uM peptide to the melanoma cells in standard 96-well culture plates. Cells were cultured in media for 4 days after seeding at about 1000 cells per well. After growth the culture media was replaced with media containing 0.5 mg/ml MTT solution and incubated for 4 hours at 37° C. The MTT solution was then removed and the residual dye was solubilized in 100 ul isopropanol for 15 minutes before reading the O.D. at 570 nm.

Scratch Assay

B16F10 melanoma cells were seeded into 24-well plates at 2×10$^5$ cells/well. After overnight growth, the wells were scratched with a yellow pipette tip and fresh media was placed on the cells. Peptide was added to treated wells at 15 uM at 12 hour intervals and images were taken with a Motic™ camera on an Olympus inverted-microscope stage.

REFERENCES

1. Turk V et al. Cystatins: biochemical and structural properties and medical relevance. Front Bioscience 13, 5406-20. 2009
2. Cai X et al. Serum Cystatin C is an early biomarker for assessment of renal function in human patients Clin. Chem Lab Med 50, 667-71. 2012
3. Cox J L Cystatins and Cancer Frontiers in Bioscience. 2009
4. Tizon B et al. Cystatin C protects neuronal cells from amyoid beta induced toxicity J Alzheimers Dis 19, 885-894. 2010
5. Cox J L et al. Inhibition of B16 melanoma metastasis by overexpression of the cysteine protease inhibitor Cystatin C Melanoma Research 9, 369-374. 1999
6. Sexton P S and Cox J L Inhibition of motility and invasion of B16 melanoma by the overexpression of Cystatin C Melanoma Research 7, 97-101. 1997
7. Ervin H and Cox, J L Late stage inhibition of hematogenous metastasis by Cystatin C over-expression Cancer Cell International 5, 14-21. 2005
8. Konduri S D et al. Modulation of Cystatin C expression impairs the invasiveness and tumorigenic potential of human glioblastoma cells Oncogene 21, 8705-12. 2002
9. Sokol J P et al. The use of Cystatin C to inhibit epithelial mesenchymal transition andmorphological transformation stimulated by transforming growth factor beta Cancer Res 7, R844-53 2005
10. Weigel B et al. Cystatin C is downregulated in prostate cancer and modulates invasion of prostate cancer cells via MAPK/Erk and androgen receptor pathways PLOS One 4, e7953 2009
11. Alvarez-Diaz S et al. Cystatin D is a candidate tumor suppressor gene induced by vitamin D in human colon cancer cells J. Clin Invest 119, 2343-58 2009
12. Ostrowski, L E et al. Selective inhibition of proteolytic enzymes in an in vivo mouse model of experimental metastasis Cancer Research 46, 4121-4128. 1986
13. Gopalakrishna R and Barsky S H tumor promoter induced membrane-bound protein kinase C regulates hematogenous metastasis PNAS 85, 612-616. 1988
14. Dissanayake S K et al. The Wnt5a/Protein kinase C pathway mediates motility in melanoma cells via the inhibition of metastasis supressors and initiation of an epithelial to mesenchymal transition J Biol Chem 282, 17259-17271. 2007
15. Kawamoto T. et al. Inhibition of PKC alpha activation in human bone and soft tissue sarcoma cells by the selective PKC inhibitor PKC412 Anticancer Research 28, 825-32 2012
16. Teno N et al. Amino acids and peptides XV. Synthesis of Gln-Val-Val-Ala-Gly and derivatives. Int. J. Peptide Res. 30, 93-98. 1987.
17. Derossi D. et al. Cell Internalization of the third helix of the Antennapedia homeodomain is receptor-independent Journal of Biological Chemistry 271, 18188-18193 1996
18. Solem M et al. Transforming growth factor beta regulates Cystatin C in serum-free mouse embryo cells BBRC 172, 945-951. 1990
19. Hakansson K et al. Mouse and rat Cystatin C: *Escerichia coli* production, characterization, and tissue distribution Comp Biochem Pysiol Biochem Mol Bio 114, 303-11. 1996
20. Turk V, and Bode W Human cysteine proteinases and their inhibitors, stefins and cystatins Chapter 4, pp 47-59. In biological functions of Proteases and Inhibitors eds. Katanuma N, Suzuki K, Travis J, and Fritz H. Karger 1994.

21. Kim J et al. Sustained inhibition of PKC alpha reduces intravasation and lung seeding during mammary tumor metastasis in an in vivo mouse model; Oncogene 30:323-33, 2011.
22. Heo k et al. Cell Penetrating H4 tail peptides potentiates p53-mediated tansactivation via inhibition of G9a and HDAC1; Oncogene 2012 doi:10.1038/onc.2012.273.
23. Chaubey B, et al. Single acute dose and repeat doses toxicity of anti-HIV-1 PNA TAR-penetratin conjugate after intraperitoneal administration to mice. Oligonucleotides 18, 9-20. 2008; Abes R et al. cell penetrating peptide based delivery of oligonucleotides: an overview Biochem Soc Trans 35:775-9. 2007.

I claim:

1. A method of treating glioblastoma, breast cancer, fibrosarcoma, prostate cancer, and melanoma, comprising the step of administering an effective amount of an isolated therapeutic Cystatin C peptide of 16 amino acids, consisting of a peptide sequence selected from the group consisting of SEQ ID NO:5, SEQ ID NO:6, SEQ ID NO:7, SEQ ID NO:8, SEQ ID NO:9, SEQ ID NO: 10, SEQ ID NO: 11, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23 to a metastatic cancer patient, wherein the tumor burden is reduced, and wherein the therapeutic Cystatin C peptide is attached to an uptake peptide.

2. The method of claim 1, wherein the therapeutic Cystatin C peptide consists of the peptide sequence selected from the group consisting of SEQ ID NO:5, SEQ ID NO:6, SEQ ID NO:7, SEQ ID NO:8, SEQ ID NO:9, SEQ ID NO: 10, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

3. The method of claim 2, wherein the therapeutic Cystatin C peptide consists of the peptide sequence selected from the group consisting of SEQ ID NO:5, SEQ ID NO:7, SEQ ID NO:8 SEQ ID NO: 12, SEQ ID NO: 13, SEQ ID NO; 14, SEQ ID NO: 15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

4. The method of claim 1, wherein the uptake peptide is a penetratin peptide.

5. The method of claim 4, wherein the penetratin peptide comprises SEQ ID NO:25.

6. The method of claim 1, wherein the therapeutic Cystatin C peptide is additionally attached to a polyethylene glycol (PEG).

7. The method of claim 1, wherein the peptide is delivered by a route selected from the group consisting of intravenous delivery, intradermal delivery, intratumoral delivery, intrathecal delivery and intramuscular delivery.

8. The method of claim 7, wherein the peptide is delivered intravenously.

9. The method of claim 1, wherein the tumor burden is reduced by at least 25% after one month of daily treatment.

10. A chemotherapeutic compound comprising an isolated Cystatin C peptide, wherein the therapeutic Cystatin C peptide consists of the peptide sequence selected from the group consisting of SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

11. The method of claim 10, wherein the therapeutic Cystatin C peptide consists of the peptide sequence selected from the group consisting of SEQ ID NO:5, SEQ ID NO:6, SEQ ID NO:7, SEQ ID NO:8, SEQ ID NO:9, SEQ ID NO: 10, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19, SEQ ID NO:20 SEQ ID NO:21, SEQ ID NO:22 and SEQ ID NO:23.

12. The method of claim 11, wherein the therapeutic Cystatin C peptide consists of the peptide sequence selected from the group consisting of SEQ ID NO:5, SEQ ID NO:7, SEQ ID NO:8, SEQ ID NO: 12, SEQ ID NO: 13, SEQ ID NO: 14, SEQ ID NO: 15, SEQ ID NO:16, SEQ ID NO:17, SEQ ID NO:18, SEQ ID NO:19, SEQ ID NO:20, SEQ ID NO:21, SEQ ID NO:22 and SEQ ID NO:23.

13. The compound of claim 10, wherein the therapeutic Cystatin C peptide is additionally attached to an uptake peptide.

14. The compound of claim 13, wherein the uptake peptide is a penetratin peptide.

15. The compound of claim 14, wherein the penetratin peptide comprises SEQ ID NO:25.

16. The compound of claim 10, wherein the therapeutic Cystatin C peptide is additionally attached to a polyethylene glycol (PEG).

* * * * *